United States Patent [19]

Linsley et al.

[11] Patent Number: 5,993,800
[45] Date of Patent: Nov. 30, 1999

[54] METHODS FOR PROLONGING THE EXPRESSION OF A HETEROLOGOUS GENE OF INTEREST USING SOLUBLE CTLA4 MOLECULES AND AN ANTICD40 LIGAND

[75] Inventors: Peter S. Linsley; Mark A. Kay; Christopher B. Wilson; Jeffrey Ledbetter; Alejandro A. Aruffo; Diane L. Hollenbaugh, all of Seattle, Wash.

[73] Assignee: Bristol-Myers Squibb Company, Princeton, N.J.

[21] Appl. No.: 08/474,210

[22] Filed: Jun. 6, 1995

Related U.S. Application Data

[63] Continuation-in-part of application No. 08/468,407, Jun. 5, 1995, abandoned.

[51] Int. Cl.$^6$ ................................................. A61K 48/00
[52] U.S. Cl. ................. 424/93.21; 435/69.1; 435/320.1; 435/325; 514/44; 424/93.1
[58] Field of Search ............... 424/93.1, 93.21; 514/2, 2.1, 44; 536/22.1; 436/85–87; 435/325, 320.1

[56] References Cited

U.S. PATENT DOCUMENTS

| | | | |
|---|---|---|---|
| 5,399,346 | 3/1995 | Anderson et al. | 424/93.21 |
| 5,693,622 | 12/1997 | Wolf et al. | 514/44 |
| 5,872,154 | 2/1999 | Wilson et al. | 514/885 |

FOREIGN PATENT DOCUMENTS 0 613 944   9/1994   European Pat. Off. .

OTHER PUBLICATIONS

Kay et al., PNAS, vol. 84, pp. 4686, 1997.
Gunzberg et al. (Molecular Medicine Today, vol. 1, pp. 410–417, 1995).
Crystal (Science, vol. 270,:404–410, 1995).
Mastrangelo et al. (Seminars in Oncology, vol. 23, No. 1:4–21, 1996).
Linsley et al. (WO 93/00431), Jul. 1993.
Kay et al. (Hepatology, vol. 21, 3:815–819, 1995).
Adam et al., "Identification of a Signal in a Murine Retrovirus that is Sufficient for Packaging of Nonretroviral RNA into Virions", *J. Virol.* 62:3802–3806 (1988) (Exhibit 2).
Algate et al., "Regulation of the Interleukin–3 (IL–3) in the Fetal Liver–derived F15.12 Cell Line", *Blood* 83(9):2459–68 (1994) (Exhibit 3).
Armentano et al., "Effect of Internal Viral Squences on the Utility of Retroviral Vectors",*J. Virol.* 61:1647–1650 (1987) (Exhibit 4).
Bachettis et al., "Transfer of Gene for Thymidine Kinase–Deficient Human Cells by Purified Herpes Simplex Viral DNA", *PNAS USA* 74:1590 (1977) (Exhibit 5).
Barr et al., "Strain Related Variations in Adenovirally Mediated Transgene Expression from Mouse Hepatocytes in Vivo: Comparisons Between Immunocompetent and Immunodeficient Inbred Strains", *Gene Therapy* 2:151–155 (1995) (Exhibit 6).

Bender et al., "Evidence that the Packaging Signal of Moloney Murine Leukemia Virus Extends into the GAG Region", *J. Virol.* 61:1639–1646 (1987) (Exhibit 7).
Berkner, K., "Development of Adenovirus Vectors for Expression of Heterologous Genes", *Biotechniques* 6:616 (1988) (Exhibit 8).
*Biochemical and Biophysical Research Communications* 199(1):26–32 (1994) (Exhibit 9).
Breviario et al., "Interleukin–1–Inducible Genes in Endothelial Cells. Cloning of a New Gene Related to C–Reactive Protein and Serum Amyloid P Component", *Journal of Biological Chemistry* 267(31):22190–7 (1992) (Exhibit 10).
Cluitmans et al., "IL–4–Down–Regulates IL–2, IL–3, and GM–CSF–Induced Cytokine Gene Expression in Peripheral Blood Monocytes", *Annals of Hematology* 68(6)293–8 (1994) (Exhibit 11).
Culver et al., "Lymphocytes as Cellular Vehicles for Gene Therapy in Mouse and Man", *PNAS USA* 88:3155 (1991) (Exhibit 12).
Culver et al., "In Vivo Gene Transfer with Retroviral Vector–Producer Cells for Treatment of Experimental Brain Tumors" Cellular Immunology Section, National Cancer Institute, National Institutes of Health, Bethesda, MD. *Science* 256:1550–1552 (1992) (Exhibit 13).
Danos et al., "Safe and Efficient Generation of Recombinant Retroviruses with Amphotropic and Ecotropic Host Ranges", *Proc. Natl. Acad. Sci. USA* 85:6460–6464 (1988) (Exhibit 14).
de Wit et al., "Differential Regulation of M–CSF and IL–6 Gene Expression in Monocytic Cells", *British Journal of Haematology,* 86(2):259–64 (1994) (Exhibit 15).
Eglitis et al., "Retroviral Vectors for Introduction of Genes into Mammalian Cells", *Biotechniques* 6:608–614 (1988) (Exhibit 16).
Englehardt et al., "Ablation of E2A in Recombinant Adenoviruses Improves Transgene Persistence and Decreases Inflammatory Response in Mouse Liver", *Proc. Natl. Acad. Sci. USA* 91:6196 (1994) (Exhibit 17).
Espinoza–Delgado et al., "Regulation of IL–2 Receptor Subunit Genes in Human Monocytes. Differential Effects of IL–2 and IFN–gamma", *Journal of Immunology* 149(9):2961–8 (1992) (Exhibit 18).
Finck et al., "Treatment of Murine Lupus with CTLA4Ig", *Science* 265:1225 (1994) (Exhibit 19).

(List continued on next page.)

*Primary Examiner*—Bruce R. Campell
*Assistant Examiner*—Dave Trong Nguyen
*Attorney, Agent, or Firm*—Mandel & Adriano

[57] ABSTRACT

The invention provides a method for enhancing the expression of a gene of interest by a cell, the cell (a) comprises a recombinant nucleic acid sequence encoding and (b) is capable of expressing the gene of interest, the method comprising contacting the cell with an amount of a soluble CTLA4 molecule effective to enhance the expression of the gene of interest by the cell.

10 Claims, 8 Drawing Sheets

OTHER PUBLICATIONS

Freireich et al., "Quantitative Comparison of Toxicity of Anticancer Agents in Mouse, Rat, Hamster, Dog, Monkey, and Man", *Cancer Chemotherapy* Re/ 50(4):219–244 (1966) (Exhibit 20).

Friedman, T. "Progress Toward Human Gene Therapy", *Science* 244:1275–1281 (1989) (Exhibit 21).

Geller et al., "An Efficient Deletion Mutant Packaging System for a Defective Herpes Simplex Virus Vectors: Potential Applications to Human Gene Therapy and Neuronal Physiology", *PNAS USA* 87:8950 (1990) (Exhibit 22).

Ghosh–Choudhury et al., "Human Adenovirus Cloning Vectors Based on Infectious Bacterial Plasmids", *Gene* 50:161 (1986) (Exhibit 23).

Gilboa et al., "Transfer and Expression of Cloned Genes Using Retroviral Vectors", *Biotechniques* 4:504–512 (1986) (Exhibit 24).

Guild et al., "Development of Retrovirus Vectors Useful for Expressing Genes in Cultured Murine Embryonic Cells and Hematopoietic Cells in Vivo", *J. Virol.* 62:795 (1988) (Exhibit 25).

Hag–Ahmand et al., "Development of Helper–Independent Human Adenovirus Vector and Its Use in the Transfer of the Herpes Simplex Virus Thymidine Kinase Gene", *J. Virol.* 57:257 (1986) (Exhibit 26).

Hock et al., "Retrovirus Mediated Transfer and Expression of Drug Resistance Genes in Human Hemopoietic Progenitor Cells", *Nature* 320:275 (1986) (Exhibit 27).

Horisberger et al., "Cloning and Sequence Analyses of cDNAs for Interferon– and Virus–Induced Human Mx Proteins Reveal that they Contain Putative Guanine Nucelotide–Binding Sites: Functional Study of the Corresponding Gene Promoter", *Journal of Virology* 64(3):1171–81 (1990) (Exhibit 28).

Karson, E., "Prospects for Gene Therapy", *Biol. Reprod.* 42:39 (1990) (Exhibit 29).

Kaufman, R., "Identification of the Component Necessary for Adenovirus Translational Control and Their Utilization in cDNA Expression Vectors", *PNAS USA* 82:689 (1985) (Exhibit 30).

Kay, et al., "Therapeutic Serum Concentrations of Human Alpha–1–Antitrypsin After Adenoviral–Medicated Gene Transfer Into Mouse Hepatocytes", *Hepatology* 1, 431 (1981) (Exhibit 31).

Kay et al., "Messenger RNA Expression of the Cytokine Gene Cluster, Interleukin 3(IL–3), IL–4, IL–5, and Granulocyte/Macrophage Colony–Stimulating Factor, in Allergen––Induced Late–Phase Cutaneous Reactions in Atopic Subjects", *Journal of Experimental Medicine*, 173(3):775–8 (1991) (Exhibit 32).

Kay et al., "In Vivo Hepatic Gene Therapy: Complete Albeit Transient Correction of Factor IX Deficiency in Hemophilia B Dogs", *Proc. Natl. Acad. Sci. USA* 91, 2353 (Exhibit 33).

Knodell et al., "Formulation and Application of a Numerical Scoring System for Assessing Histological Activity in Asymptomatic Chronic Alive Hepatitis", *Hepatology* 1, 431 (Exhibit 34).

Lagoo et al., "IL–2, IL–4 and IFN–gamma Gene Expression Versus Secretion in Superantigen–Activated T Cells. Distinct Requirement for Costimulatory Signals Through Adhesion Molecules", *Journal of Immunology* 152(4):1641–52 (1994) (Exhibit 35).

Lewis, et al., "Interleukin 4 Expressed In Situ Selectively Alters Thymocyte Development", *J. Exp. Med.* 173:89–100 (1991) (Exhibit 36).

Li et al., "Assessment of Recombinant Adenoviral Vectors for Hepatic Gene Therapy", *Human Gene Therapy* 4, 403 (1993) (Exhibit 37).

Li et al., "Proinflammatory Cytokines Tumor Necrosis Factor–alpha and IL–6 but not IL–1, Down–Regulate the Osteocalcin Gene Promoter", *Journal of Immunology* 148(3):788–794 (1992) (Exhibit 38).

Linsley et al., "Binding of the B Cell Activation Antigen B7 to CD28 Costimulates T Cell Proliferation and Interleukin 2 mRNA Accumulation", *J. Exp. Med.* 173:721–730 (1991) (Exhibit 39).

Linsley et al., "Immunosuppression in Vivo by a Soluble Form of the CTLA4 Cell Activation Molecule", *Science* 257(5071)792–795 (1992) (Exhibit 40).

Linsley et al., "The Role of the CD28 Receptor During T Cell Responses to Antigen", *Annu. Rev. Immunol.* 11:191–212 (1993). (Exhibit 41).

Markowitz et al., "Construction and Use of a Safe and Efficient Amphotropic Packaging Cell Line", *Virology* 167:400–406 (1988) (Exhibit 42).

Martinez et al., Il–2 and Il–5 Gene Expression in Response to Alloantigen in Liver Allograft Recipients and in Vitro, *Transplantation* 55(5):1159–66 (1993) (Exhibit 43).

Mauviel et al., "Leukoregulin, A T Cell–Derived Cytokine, Induces Il–8 Gene Expression and Secretion in Human Skin Fibroblasts", *Journal of Immunology* 149(9):2969–76 (1992) (Exhibit 44).

Miller, Dusty A., "Progress Toward Human Gene Therapy", *Blood* 76:271–278 (1990) (Exhibit 45).

Miller et al., "Redesign of Retrovirus Packaging Cell Lines to Avoid Recombination Leading to Helper Virus Production", *Molecule and Cellular Biology* 6:2895–2902 (1986) (Exhibit 46).

Miller et al., "Improved Retroviral Vectors for Gene Transfer and Expression", *Biotechniques* 7:980–986 (1989) (Exhibit 47).

Miller et al., "Factors Involved in Production of Helper Virus–Free Retrovirus Vectors", *Somatic Cell Mol. Genet.* 12:175–183 (1986) (Exhibit 48).

Mukhopadhyay, et al., "Specific Inhibition of K–ras Expression and Tumorigenicity of Lung Cancer Cells by Antisense RNA", *Cancer Res.* 51:1744–1748 (1991) (Exhibit 49).

Nguyen, et al., "Mechanism of Virus–Induced Ig Subclass Shifts", *J. Immunol.* 152:478–484 (1994) (Exhibit 50).

Nonoyama et al., "Strain–Dependent Leakiness of Mice with Severe Combined Immune Deficiency", *J. Immunol.* 150:3817–3824 (1993) (Exhibit 51).

Nonoyama, et al., "B Cell Activation via CD40 Is Required for Specific Antibody Production by Antigen–Stimulated Human B Cells", *J. Exp. Med.* 178:1097–1102 (1993) (Exhibit 52).

Pang et al., "GM–CSF, IL–1α, IL–1β, IL–6, IL–8, IL–10, ICAM–1 and VCAM–1 Gene Expression and Cytokine Production in Human Duodenal Fibroblasts Stimulated with Lipopolysaccharide, IL–1α and TNF–α", *Clin. Exp. Immunol.* 96:437–443 (1994) (Exhibit 53).

Panicali, et al., "Construction of Poxviruses as Cloning Vectors: Insertion of the Thymidine Kinase Gene from Herpes Simplex Virus into the DNA of Infectious Vaccinia Virus", *Proc. Natl. Acad., Sci. USA* 79:4927–4931 (1982) (Exhibit 54).

Pizarro, et al., "Induction of TNFα and TNF β Gene Expression in Rat Cardiac Transplants During Allograft Rejection", *Transplantation* 56:399–404 (1993) (Exhibit 55).

Rosenfeld, et al., "Adenovirus–Mediated Transfer of a Recominant α1–Antitrypsin Gene to the LUng Epithelium in Vivo", *Science* 252:431–434 (1991) (Exhibit 56).

Roth, et al., "Molecular Approaches to Prevention and Therapy of Aerodigestive Tract Cancers", *Monogr. Natl. Cancer Inst.* 13:15–21 (1992) (Exhibit 57).

Sarver, et al., "Bovine Papilloma Virus Deoxyribonucleic Acid: a Novel Eucaryotic Cloning Vector", *Molecular and Cellular Biology* 1:486–496 (1981) (Exhibit 58).

Smith et al., "Infectious Vaccinia Virus Recombinants that Express Hepatitis B Virus Surface Antigen", *Nature* 302:490–495 (1983) (Exhibit 59).

Smith et al., "Adenovirus Mediated Expression of Therapeutic Plasma Levels of Human Factor IX in Mice", *Nature Genetics* 5:397–402 (1993) (Exhibit 60).

Sprecher et al., "Detection of IL–1β, TNF–α, and IL–6 Gene Transcription by the Polymerase Chain Reaction in Keratinocytes, Langerthans Cells and Peritoneal Exudate Cells During Infection with Herpes Simplex Virus–1", *Arch. Viol.* 126:253–269 (1992) (Exhibit 61).

Ulich et al., "Endotoxin–Induced Cytokine Gene Expression in Vivo III. Il–6 mRNA and Serum Protein Expression and the in Vivo Hematologic Effects of IL–6", *Journal of Immunology* 146:2316–2323 (1991) (Exhibit 62).

Verma, IM, "Gene Therapy", *Sci. Am.* 263:68 (1990) (Exhibit 63).

Paul et al., "Lymphocyte Responses and Cytokines", *Cell* 76:241–251 (1994) (Exhibit 64).

Wong et al., "Human GM–CSF: Molecular Cloning of the Complementary DNA and Purification of the Natural and Recombinant Proteins", *Science* 228:810–815 (1985) (Exhibit 65).

Yang et al., "MHC Class I–Restricted Cytotoxic T Lymphocytes to Viral Antigens Destroy Hepatocytes in Mice Infected with E1–Deleted Recombinant Adenoviruses", *Immunity* 1:443–442 (1994) (Exhibit 66).

Yang et al., "Cellular Immunity to Viral Antigens Limits E1–deleted Adenoviruses for Gene Therapy", *Proc. Natl. Acad. Sci.* 91:4407–4411 (1994) (Exhibit 67).

METHODS FOR PROLONGING THE EXPRESSION OF A HETEROLOGOUS GENE OF INTEREST USING SOLUBLE CTLA4 MOLECULES AND AN ANTICD40 LIGAND

CROSS-REFERENCE TO RELATED APPLICATIONS

This application is a continuation in part of U.S. Ser. No. 08/468,407, filed Jun. 5, 1995, now abandoned, the contents of which are incorporated by reference into the present application.

Gene therapy holds great promise for the treatment of many diseases that now lack specific therapies (Friedmann T. Progress toward human gene therapy. Science 1989;244:1275; Verma I M. Gene therapy. Sci Am 1990;263:68; Miller A D. Progress toward human gene therapy. Blood 1990;76:271; Karson, E M. Prospects for gene therapy. Biol Reprod 1990;42:39).

For example, human cancer is often associated with aberrant gene expression or mutations in specific genes, and it is possible that neoplastic processes can be altered by gene therapy. Alternatively, tumor cells altered by gene therapy may be destroyed by the insertion of toxic genes or genes rendering them sensitive to chemotherapeutic agents. Another approach to inactivating neoplastic cells is to insert an antisense oncogene into the tumor cells. These genes are transcribed in the reverse orientation to the oncogene. Because the sequences are complementary, the mRNAs hybridize; the oncogene activity is depleted because the gene cannot be translated (Friedmann T. Progress toward human gene therapy. Science 1989;244:1275).

Bone marrow is a suitable target site for gene therapy, because it is readily accessible and manipulable in vitro and contains stem cells to perpetuate the altered genotype. Liver and the central nervous system are also potential targets for gene therapy (Miller A D. Progress toward human gene therapy. Blood 1990;76:271).

The primary goal of gene therapy is to introduce additional genetic elements into a living cell or to replace missing or nonfunctional molecular elements in the DNA of a living cell so as to target and repair alterations within living cells that lead to disease in man (Culver et al., Lymphocytes as cellular vehicles for gene therapy in mouse and man, PNAS USA, 88:3155 (1991)).

Depending on the disease being treated, three strategies for gene therapy may be adopted. Dysfunctional genes may be replaced, altered to become functional, or augmented with healthy genes working at different loci within the cell. of these options, gene augmentation therapy is currently the most feasible. An example of gene augmentation is the addition of a functional adenosine deaminase gene to cells from patients with severe combined immunodeficiency (Friedmann T. Progress toward human gene therapy. Science 1989;244:1275; Verma I M. Gene therapy. Sci Am 1990;263:68; Miller A D. Progress toward human gene therapy. Blood 1990;76:271; Karson, E M. Prospects for gene therapy. Biol Reprod 1990;42:39).

Prerequisites for gene therapy are understanding the defect of the disease and having a normal functional gene cloned and characterized. Genes are introduced by several methods.

Gene therapy may involve transferring genes into cells in culture and then transplanting the cultured cells into a subject (ex vivo approach) or directly delivering genes into a subject for in situ gene transfer into cells (in vivo approach).

In both the in vivo and ex vivo approach, virus vectors have been exploited as delivery vehicles for the genes of interest. The viral genomes are altered to render them nonvirulent but capable of infecting certain cell types. An advantage of retroviral vectors is the fact that the introduced DNA is efficiently integrated into the host chromosome. The functional replacement gene is inserted in a position within the viral genome to render it capable of being expressed after it has entered the appropriate tissue. The virus is then administered to the patient or the target cells to allow transformation to the desired functional phenotype. A disadvantage of retroviral vectors is the need for cell replication for efficient gene transfer. In contrast, adenovirus vectors do not require cell replication, but the introduced DNA is not integrated into the host chromosome.

These recombinant viral vectors, including adenovirus vectors, are efficient at transferring genes into somatic tissues but are limited for use in clinical gene therapy by immunologic factors that result in the rapid loss of gene expression and inhibit secondary gene transfer. Specifically, gene expression is transient, generally lasting no more than several weeks because of a cellular immune response directed against transduced cells (Y. Yang et al. (1994) *Proc. Natl. Acad. Sci., USA* 91, 4407; Y. Yang, H. C. J. Ertl, J. M. Wilson (1994) *Immunity* 1, 433). This limitation may be circumvented by using soluble CTLA4 molecules which result in prolonging gene expression.

CTLA4 is a cell surface antigen normally found on T cells. CTLA4 binds to the B cell activation antigen B7. A soluble CTLA4 molecule, i.e., CTLA4Ig, has been shown to inhibit immune responses dependent on the interaction between T and B cells (Linsley et al, *J. Exp. Med.* 173:721–730 (1991).

The use of soluble CTLA4 molecules in immunotherapy greatly enhances the likelihood that recombinant viral vectors will be useful for human gene therapy.

SUMMARY OF THE INVENTION

The present invention is directed to a method for prolonging the expression of a gene of interest by a cell. In this method, the cell comprises a recombinant nucleic acid sequence encoding the gene of interest and is capable of expressing the gene of interest. This method provides the step of contacting the cell with an amount of a soluble CTLA4 molecule effective to prolong the expression of the gene of interest by the cell. Alternatively, when the cell is located in a subject, the method comprises administering to the subject an amount of soluble CTLA4 molecule, which effectively prolongs the expression of the gene of interest by the cell.

The present invention also provides a method for treating a subject suffering from a disease. In accordance with the method, at least one cell of the subject (a) comprises a recombinant nucleic acid sequence for a gene of interest and (b) is capable of expressing the protein encoded by gene of interest that is capable of inhibiting the disease or symptoms associated therewith. This method comprises administering to the subject an amount of a soluble CTLA4 effective to enhance the amount or duration of expression of the gene: of interest by the subject.

BRIEF DESCRIPTION OF THE FIGURES

FIGS. 1A–B are line graphs showing adenovirus mediated gene expression with coadministration of soluble CTLA4Ig. Each line represents an individual animal. FIGS. 1C–D are line graphs showing serum concentrations of soluble CTLA4Ig in the animals depicted in FIGS. 1A–B, respectively.

FIGS. 2A–C are line graphs showing the results of spleen proliferation assays.

FIG. 3 is a photograph identifying hepatic inflammatory cells through immunohistochemistry.

DETAILED DESCRIPTION OF THE INVENTION

DEFINITION

Figure 1A:
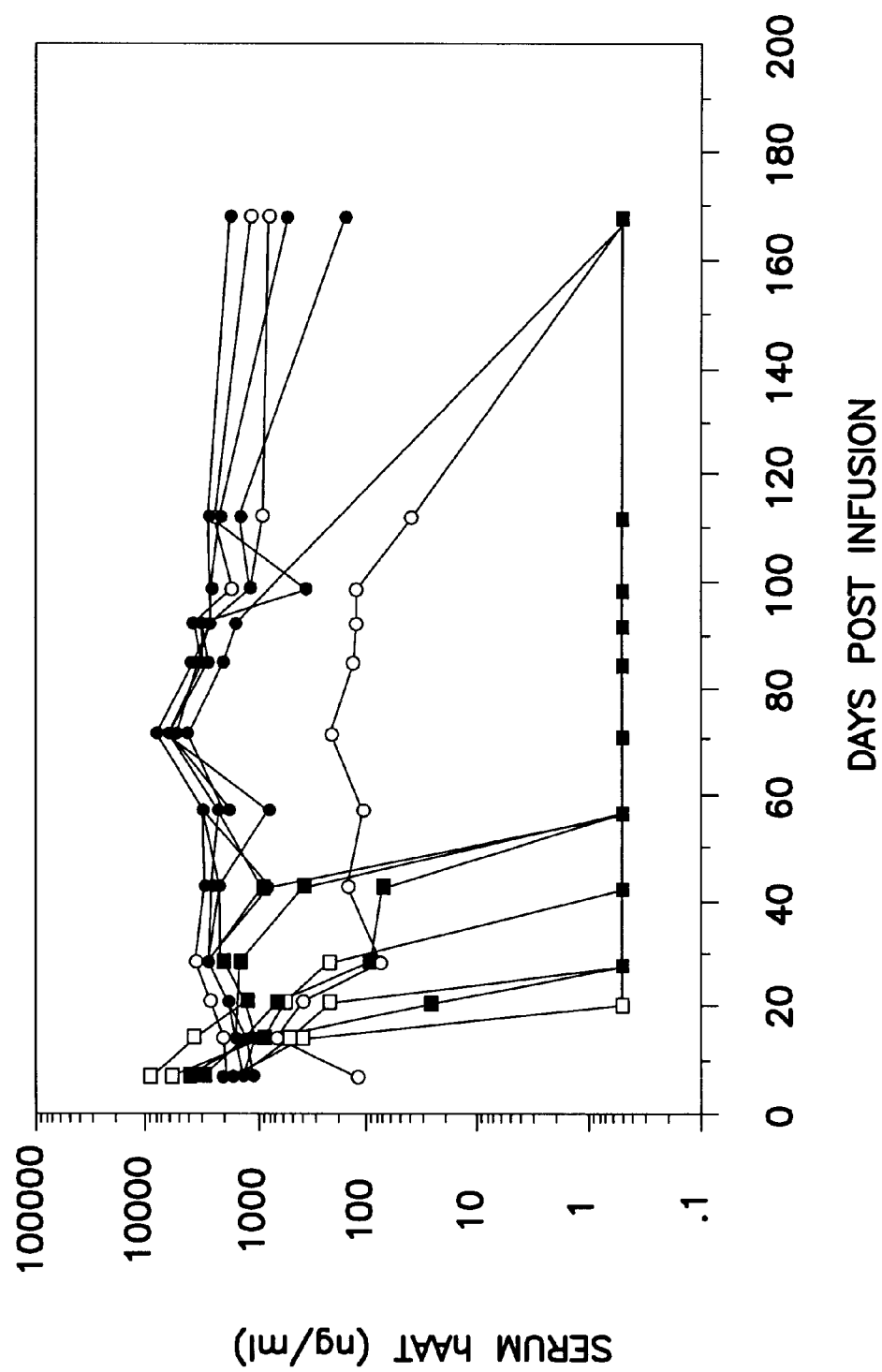

As used in this application, the following words or phrases have the meanings specified.

As used herein a "gene of interest" means any DNA or RNA molecule which encodes a protein or nucleic acid sequence.

As used herein a "non-CTLA4 protein sequence" means any molecule which does not bind B7 and does not interfere with the binding of CTLA4 to its B7 antigen target.

As used herein "the extracellular domain of CTLA4" is any portion of CTLA4 which recognizes and binds the B7 antigen. For example, an extracellular domain of CTLA4 is described in Linsley et al., J. Exp. Med. 173:721–730 (1991); Linsley et al. "Immunosuppression in vivo by a soluble form of the CTLA4 cell activation molecule" Science (1992) 257(5071)792–795.

As used herein "soluble CTLA4" means a circulating CTLA4 capable of binding to B7. Examples include but are not limited to the extracellular domain of CTLA4 or the extracellular domain of CTLA4 fused (genetically or chemically) to a biologically or chemically active molecule such as CTLA4Ig, CTLA4-env gp120, CTLA4-p97, CTLA4-ova, and CTLA4-E7.

As used herein "gene therapy" is a process to correct a disease by genetic manipulation.

As used herein "viral vector" is a carrier nucleic acid molecule (1) into which a gene of interest can be inserted for introduction into a host cell where it will be expressed and (2) which is derived from a virus.

In order that the invention herein described may be more fully understood, the following description is set forth.

METHODS OF THE INVENTION

This invention relates to the discovery that an effective amount of soluble CTLA4 enhances the expression of a gene of interest by a cell by permitting its prolonged or persistent gene expression. In a preferred embodiment of the invention, the gene of interest is part of a recombinant nucleic acid sequence such as a recombinant viral vector. Recombinant viral vectors are described herein.

In one embodiment of the invention, enhancement of gene expression is effected by contacting the cell with an amount of the soluble CTLA4 molecule so as to inhibit an immune response. Alternatively, enhancement of gene expression is effected by administering to a subject an amount of a soluble CTLA4 so as to inhibit an immune response thereby achieving persistent viral gene expression without long-term immunosuppression. Additionally, the combination of a soluble CTLA molecule and an MR1 antibody prolongs gene expression and allows secondary gene transfer.

Soluble CTLA4 molecules may be administered during gene therapy, before gene therapy, or after gene therapy. Further, administration of soluble CTLA4 is useful even after subsequent administrations of genes through in vivo or ex vivo approaches. The use of soluble CTLA4 molecules may allow successful secondary gene expression following a second administration of a gene of interest through in vivo or ex vivo approaches that normally would not be possible because of an immune response.

Soluble CTLA4 may be administered by oral means, transdermal means, intravenous means, intramuscular means, or by subcutaneous administration. Alternatively, CTLA4 may be inserted together with the gene of interest in a viral vector and co-expressed.

The methods of the invention are useful in treating a subject suffering from defective, diseased or damaged cells. In particular, use of soluble CTLA4 can augment gene therapies in patients suffering from a disease (U.S. Pat. No. 5,399,346, issued Mar. 21, 1995). The likelihood of success in gene is therapy is improved as a result of the enhancement of gene expression and the subject who is suffering from a disease is treated more effectively than without the use of soluble CTLA4 before, after, and/or during gene therapy.

In one embodiment of the invention, at least one cell in the subject must comprise recombinant DNA for a gene of interest. Further, the cell must be capable of expressing the protein encoded by that gene of interest so that disease or symptoms associated therewith are inhibited.

In accordance with the practice of the invention, the subject may be an animal subject such as a human, a dog, a cat, a sheep, a horse, a fish, a bird, a pig, or a cow.

Presently, several groups are using gene therapy in cancer treatment (Friedmann T. Progress toward human gene therapy. Science 1989; 244:1275–1281; Roth J A, Mukhopadhyay T, Tainsky M A, et al. Molecular approaches to prevention and therapy of aerodigestive tract cancers. Review article. Monogr Natl Cancer Inst 1992; 13:15–21; Mukhopadhyay T, Tainsky M, Cavender A C, Roth J A. Specific inhibition of K-ras expression and tumorigenicity of lung cancer cells by antisense RNA. Cancer Res 1991; 51:1744–1748).

Researchers have developed protocols for the treatment of experimental brain tumors by directly injecting cells producing retroviral particles carrying the herpes thymidine kinase (TK) gene into brain cancers (Culver K W, Ram Z, Wallbridge S, et al. In vivo gene transfer with retroviral vector-producer cells for treatment of experimental brain tumors, Cellular Immunology Section, National Cancer Institute, National Institutes of Health, Bethesda, M D. Science 1992; 256:1550–1552). The incorporation of the TK gene into tumor cells will make them sensitive to the drug ganciclovir. Use of soluble CTLA4 may enhance the expression of the TK gene.

The invention further provides a method for treating defective, diseased or damaged cells in a subject comprising inserting the Ad/RSV-CTLA4Ig (mu) -BPA or Ad/RSV-CTLA4Ig(hu) -BPA vector into cells so that the cells produce the protein encoded by the gene of interest together with soluble CTLA4 molecules in a sufficient amount to ameliorate the defective, diseased or damaged cells in the central nervous system.

The invention further provides a method for treating defective, diseased or damaged cells in a subject comprising grafting donor cells into the subject. In accordance with the practice of the invention, the donor cells are genetically modified. Specifically, such donor cells are inserted with the Ad/RSV-CTLA4Ig(mu) -BPA or Ad/RSV-CTLA4Ig(hu) -BPA so that such donor cells produce the protein encoded by the gene of interest together with soluble CTLA4 molecules in a sufficient amount to ameliorate the defective, diseased or damaged cells.

CELLS

The cells which include the gene of interest may be any eucaryotic cell such as epithelial cells and connective cells.

Epithelial cells are located on every surface area of the animal body, even internal areas such as the inner wall of a blood vessel or of the stomach. Connective cells include cells which make up bone tissue, cartilage tissue and blood, i.e., both white and red blood cells. The cell comprises recombinant DNA encoding and is capable of expressing the gene of interest in vitro and in vivo.

The cell may be an animal cell such as a cell from a human, a dog, a cat, a sheep, a horse, a fish, a bird, a pig, or a cow.

The donor cells may be producer cells. Further, the donor cells may be autologous or heterologous cells.

INTRODUCTION OF FOREIGN GENES INTO CELLS

A variety of techniques are available for the introduction of DNA or RNA into cells. Generally, gene therapy involves (1) transferring genes into cells in culture and then transplanting the cultured cells into a subject (ex vivo approach) or (2) directly delivering genes into a subject for in situ gene transfer into cells (in vivo approach).

For example, the gene of interest may be inserted into a cell directly in a recombinant viral vector. Other insertion methods are possible.

For example, in ex vivo techniques, the gene can be inserted into a cell using any gene transfer procedure such as calcium phosphate mediated transfection, the use of polycations or lipids complexed with DNA, encapsulation of DNA in lipid vesicles or erythrocyte ghosts, or the exposure of cells to rapid pulses of high voltage electric current (i.e., electroporation). DNA has also been introduced into cells by direct microinjection or by the use of high-velocity tungsten microprojectiles. These techniques are capable of integrating multiple copies of DNA into the genome although the efficiency of the integration varies widely with the technique, different genes, and different cell types.

Recently techniques have been developed using viral vectors to introduce DNA into mammalian cells. These techniques have the potential for infecting all cells exposed to the virus. In developing techniques for the use of viral vectors, it was necessary to develop vectors that stably incorporated into the target cell without damaging it.

Suitable viral vectors include papovaviruses, simian virus 40, polyomavirus, adenoviruses, murine and avian retroviruses. Viral vectors can infect multiple cell types.

VECTORS

Compared to vectors that do not enter cells by receptor mediated events, viral vectors are preferred because of their efficiency. Examples of suitable viral vectors include, but are not limited to, a retrovirus vector, an adenovirus vector, a vaccinia virus vector, a herpes virus vector, or a rabies virus vector.

The viral vector selected should meet the following criteria: 1) the vector must be able to infect the cells of interest and thus viral vectors having an appropriate host range must be selected; 2) the transferred gene should be capable of persisting and being expressed in a cell for an extended period of time; and 3) the vector should be safe to the host and cause minimal cell transformation. Retroviral vectors and adenoviruses offer an efficient, useful, and presently the best-characterized means of introducing and expressing foreign genes efficiently in mammalian cells. These vectors have very broad host and cell type ranges, express genes stably and efficiently. The safety of these vectors has been proved by many research groups. In fact many are in clinical trials.

Other virus vectors that may be used for gene transfer into cells for correction of disorders include herpes virus papovaviruses such as JC, SV40, polyoma; Epstein-Barr Virus (EBV); papilloma viruses, e.g. bovine papilloma virus type I (BPV); poliovirus and other human and animal viruses.

Adenoviruses have several properties that make them attractive as cloning vehicles (Bachettis et al.: Transfer of gene for thymidine kinase-deficient human cells by purified herpes simplex viral DNA. *PNAS USA*, 1977 74:1590; Berkner, K. L.: Development of adenovirus vectors for expression of heterologous genes. *Biotechniaues*, 1988 6:616; Ghosh-Choudhury G, et al., Human adenovirus cloning vectors based on infectious bacterial plasmids. *Gene* 1986; 50:161; Hag-Ahmand Y, et al., Development of a helper-independent human adenovirus vector and its use in the transfer of the herpes simplex virus thymidine kinase gene. *J Virol* 1986; 57:257; Rosenfeld M, et al., Adenovirus-mediated transfer of a recombinant $\alpha_1$-antitrypsin gene to the lung epithelium in vivo. *Science* 1991; 252:431).

For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adeioviruses can be used as high level transient expression vectors with an expression period of weeks to several months. Extensive biochemical and genetic studies suggest that it is possible to substitute up to 7–7.5 kb of heterologous sequences for native adenovirus sequences generating viable, conditional, helper-independent vectors (Kaufman R. J.; identification of the component necessary for adenovirus translational control and their utilization in cDNA expression vectors. *PNAS USA*, 1985 82:689).

AAV is a small human parvovirus with a single stranded DNA genome of approximately 5 kb. This virus can be propagated as an integrated provirus in several human cell types. AAV vectors have several advantage for human gene therapy. For example, they are trophic for human cells but can also infect other mammalian cells; (2) no disease has been associated with AAV in humans or other animals; (3) integrated AAV genomes appear stable in their host cells; (4) there is no evidence that integration of AAV alters expression of host genes or promoters or promotes their rearrangement; (5) introduce genes can be rescued from the host cell by infection with a helper virus such as adenovirus.

HSV-1 vector system facilitates introduction of virtually any gene into non-mitotic cells (Geller et al. an efficient deletion mutant packaging system for a defective herpes simplex virus vectors: Potential applications to human gene therapy and neuronal physiology. *PNAS USA*, 1990 87:8950).

Another vector for mammalian gene transfer is the bovine papilloma virus-based vector (Sarver N, et al., Bovine papilloma virus DNA: A novel eukaryotic cloning vector. *Mol Cell Biol* 1981; 1:486).

Vaccinia and other poxvirus-based vectors provide a mammalian gene transfer system. Vaccinia virus is a large double-stranded DNA virus of 120 kilodaltons (kd) genomic size (Panicali D, et al., Construction of poxvirus as cloning vectors: Insertion of the thymidine kinase gene from herpes simplex virus into the DNA of infectious vaccine virus. *Proc Natl Acad Sci USA* 1982; 79:4927; Smith et al. infectious vaccinia virus recombinants that express hepatitis B virus surface antigens. *Nature*, 1983 302:490.)

Retroviruses efficiently insert viral genes into host cells (Guild B, et al., Development of retrovirus vectors useful for expressing genes in cultured murine embryonic cells and hematopoietic cells in vivo. *J Virol* 1988; 62:795; Hock R A, et al., Retrovirus mediated transfer and expression of drug resistance genes in human hemopoietic progenitor cells. *Nature* 1986; 320:275; Kriegler M. Gene transfer and expression. A laboratory manual. New York: Stockton Press, 1990:1–242; Gilboa E, Eglitis M A, Kantoff P W, et al. Transfer and expression of cloned genes using retroviral vectors. Biotechniques 1986; 4:504–512; Eglitis A M, Anderson W F. Retroviral vectors for introduction of genes into mammalian cells. Biotechniques 1988; 6:608–614; Adam M A, Miller A D. Identification of a signal in a murine retrovirus that is sufficient for packaging of nonretroviral RNA into virions. J Virol 1988; 62:3802–3806; Armentano D, Yu S F, Kantoff P W, et al. Effect of internal viral sequences on the utility of retroviral vectors. J Virol 1987; 61:1647–1650; Bender M A, Palmer T D, Gelinas R E, et al. Evidence that the packaging signal of Moloney murine leukemia virus extends into the gag region. J Virol 1987; 61:1639–1646; Danos O, Mulligan R C. Safe and efficient generation of recombinant retroviruses with amphotropic and ecotropic host ranges. Proc Natl Acad Sci USA 1988; 85:6460–6464; Markowitz D, Goff S, Bank A. Construction and use of a safe and efficient amphotropic packaging cell line. Virol 1989; 167:400–406; Miller A D, Buttimore C. Redesign of retrovirus packaging cell lines to avoid recombination leading to helper virus production. Mol Cell Biol 1986; 6:2895–2902; Miller A D, Trauber D R, Buttimore C. Factors involved in the production of helper virus-free retrovirus vectors. Somatic Cell Mol Genet 1986; 12:175–183; Miller A D, Rosman G J. Improved retroviral vectors for gene transfer and expression. Biotechniques 1989; 7:980–986).

GENE OF INTEREST

The gene of interest may be any gene of interest. The gene product from the gene of interest includes proteins or nucleic acid sequences such as sense or anti-sense molecules.

For example, the gene of interest may encode a protein selected from the group consisting of cytokines, enzymes, antibiotics, toxins, antimetabolites and precursors thereof. Suitable cytokines include interferons, GM-CSF interleukins, tumor necrosis factor (TNF) (Wong G, et al., Human GM-CSF: Molecular cloning of the complementary DNA and purification of the natural and recombinant proteins. *Science* 1985; 228:810); WO9323034 (1993); Horisberger M A, et al., Cloning and sequence analyses of cDNAs for interferon- and virus-induced human Mx proteins reveal that they contain putative guanine nucleotide-binding sites: functional study of the corresponding gene promoter. *Journal of Viroloqy*, March, 1990, 64(3):1171–81; Li Y P et al., Proinflammatory cytokines tumor necrosis factor-alpha and IL-6, but not IL-1, down-regulate the osteocalcin gene promoter. *Journal of Immunology*, Feb. 1, 1992, 148(3) :788–94; Pizarro T T, et al. Induction of TNF alpha and TNF beta gene expression in rat cardiac transplants during allograft rejection. *Transplantation*, August, 1993, 56(2) :399–404). (Breviario F, et al., Interleukin-1-inducible genes in endothelial cells. Cloning of a new gene related to C-reactive protein and serum amyloid P component. *Journal of Biological Chemistry*, Nov. 5, 1992, 267(31):22190–7; Espinoza-Delgado I, et al., Regulation of IL-2 receptor subunit genes in human monocytes. Differential effects of IL-2 and IFN-gamma. *Journal of Immunology*, Nov. 1, 1992, 149(9):2961–8; Algate P A, et al., Regulation of the interleukin-3 (IL-3) receptor by IL-3 in the fetal liver-derived FL5.12 cell line. *Blood*, May 1, 1994, 83(9) :2459–68; Cluitmans F H, et al., IL-4 down-regulates IL-2, IL-3-, and GM-CSF-induced cytokine gene expression in peripheral blood monocytes. *Annals of Hematology*, Jun. 1994, 68(6):293–8; Lagoo, A S, et al., IL-2, IL-4, and IFN-gamma gene expression versus secretion in superantigen-activated T cells. Distinct requirement for costimulatory signals through adhesion molecules. *Journal of Immunology*, Feb. 15, 1994, 152(4):1641–52; Martinez O M, et al., IL-2 and IL-5 gene expression in response to alloantigen in liver allograft recipients and in vitro. *Transplantation*, May 1993, 55(5):1159–66; Pang G, et al., GM-CSF, IL-1 alpha, IL-1 beta, IL-6, IL-8, IL-10, ICAM-1 and VCAM-1 gene expression and cytokine production in human duodenal fibroblasts stimulated with lipopolysaccharide, IL-1 alpha and TNF-alpha. *Clinical and Experimental Immunology*, June 1994, 96(3):437–43; Ulich T R, et al., Endotoxin-induced cytokine gene expression in vivo. III. IL-6 mRNA and serum protein expression and the in vivo hematologic effects of IL-6. *Journal of Immunology*, Apr. 1, 1991, 146(7):2316–23; Mauviel A, et al., Leukoregulin, a T cell-derived cytokine, induces IL-8 gene expression and secretion in human skin fibroblasts. Demonstration and secretion in human skin fibroblasts. Demonstration of enhanced NF-kappa B binding and NF-kappa B-driven promoter activity. *Journal of Immunology*, Nov. 1, 1992, 149(9):2969–76).

Growth factors include Transforming Growth Factor-α (TGFα) and β (TGFβ), cytokine colony stimulating factors (Shimane M, et al., Molecular cloning and characterization of G-CSF induced gene cDNA. *Biochemical and Biophysical Research Communications*, Feb. 28, 1994, 199(1) :26–32; Kay A B, et al., Messenger RNA expression of the cytokine gene cluster, interleukin 3 (IL-3), IL-4, IL-5, and granulocyte/macrophage colony-stimulating factor, in allergen-induced late-phase cutaneous reactions in a topic subjects. *Journal of Experimental Medicine*, Mar. 1, 1991, 173(3):775–8; de Wit H, et al., Differential regulation of M-CSF and IL-6 gene expression in monocytic cells. *British Journal of Haematology*, Febrary, 1994, 86(2):259–64; Sprecher E, et al., Detection of IL-1 beta, TNF-alpha, and IL-6 gene transcription by the polymerase chain reaction in keratinocytes, Langerhans cells and peritoneal exudate cells during infection with herpes simplex virus-1. *Archives of Virology*, 1992, 126(1–4):253–69).

Suitable enzymes include thymidine kinase (TK), xanthine-guanine phosphoribosyltransferase (GPT) gene from *E. coli* or *E. coli* cytosine deaminase (CD), or hypoxanthine phosphoribosyl transferase (HPRT).

Suitable oncogenes and tumor suppressor genes include neu, EGF, ras (including H, K, and N ras), p53, Retinoblastoma tumor suppressor gene (Rb), Wilm's Tumor Gene Product, Phosphotyrosine Phosphatase (PTPase), and nm23. Suitable toxins include Pseudomonas exotoxin A and S; diphtheria toxin (DT); *E. coli* LT toxins, Shiga toxin, Shiga-like toxins (SLT-1, -2), ricin, abrin, supporin, and gelonin.

DOSAGES OF SOLUBLE CTLA4 MOLECULES

The most effective mode of administration and dosage regimen for the molecules of the present invention depends upon the location of the tissue or disease being treated, the severity and course of the medical disorder, the subject's health and response to treatment and the judgment of the treating physician. Accordingly, the dosages of the molecules should be titrated to the individual subject.

The interrelationship of dosages for animals of various sizes and species and humans based on mg/m² of surface area is described by Freireich, E. J., et al. Cancer Cherrother., Rep. 50 (4): 219–244 (1966). Adjustments in the dosage regimen may be made to optimize the tumor cell growth inhibiting and killing response, e.g., doses may be divided and administered on a daily basis or the dose reduced proportionally depending upon the situation (e.g., several divided does may be administered daily or proportionally reduced depending on the specific therapeutic situation).

In accordance with the practice of the invention an effective amount for treating a subject may be between about 0.1 and about 10 mg/kg body weight of subject. Also, the effective amount may be an amount between about 1 and about 10 mg/kg body weight of subject.

It would be clear that the dose of the composition of the invention required to achieve cures may be further reduced with schedule optimization.

SOLUBLE CTLA4 MOLECULES

Examples of soluble CTLA4 includes CTLA4Ig, any functional portion of a CTLA4 molecule which binds a B7 antigen expressed on activated B cells. For example, the functional CTLA4 molecule comprises the 187 amino acids shown in SEQ ID NO 14 beginning with alanine at position 1 and ending with asparagine at position 187. Alternatively, the functional CTLA4 molecule comprises the 125 amino acids shown in SEQ ID NO 13 beginning with alanine at position 1 and ending with asparagine at position 125 of the amino acid sequence of the extracellular domain of the CTLA4 protein.

The functional CTLA4 molecule may be joined to a non-CTLA4 protein sequence such as a portion of an immunoglobulin molecule. Examples of soluble CTLA4 molecules include soluble CTLA4-p97 molecule; soluble CTLA4-env gp120 molecule; soluble CTLA4-E7 molecule; and soluble CTLA4-ova molecule.

In one embodiment the soluble CTLA4 molecule is CTLA4Ig having the amino acid sequence corresponding to the CTLA4Ig fusion protein has been deposited with the American Type Culture Collection (ATCC) in Rockville, Md., under the provisions of the Budapest Treaty on May 31, 1991 and has been accorded ATCC accession number: 68629.

ADVANTAGES OF THE INVENTION

Gene therapy is a novel form of molecular medicine that will have a major impact on human health in this and the next century. Gene therapy has the possibility of correcting inherited genetic disorders like cystic fibrosis, hemophilia, familial hypercholesterolemia, cancer, AIDS, Parkinson's disease, Alzheimer's disease, and infectious diseases.

Recombinant viral vectors are attractive vehicles for gene therapy because they are efficient at transferring genes into somatic tissues. However, before applicants' invention, their use was limited in clinical gene therapy because transgene expression becomes transient over time. Further, circumventing transient expression through a second or subsequent administration of the virus results in significantly reduced gene transfer.

Applicants' discovery lies in the finding that administration of soluble CTLA4Ig, before, after, or during in vivo or ex vivo gene transfer into cells, results in persistent gene expression by the recombinant viral vector in the subject without long-term immunosuppression.

The following examples are presented to illustrate the present invention and to assist one of ordinary skill in making and using the same. The examples are not intended in any way to otherwise limit the scope of the invention.

EXAMPLE 1

This experiment determined that the use of soluble CTLA4Ig molecules results in prolonged gene expression after adenovirus mediated gene transfer.

All animal studies were performed in accordance with the institutional guidelines set forth by the University of Washington. All animals were housed in specific pathogen free facilities (SPF).

Mice (e.g., C3H/HeJ mice) were injected with recombinant adenovirus diluted to 100 μl in DMEM media (Hyclone) by tail vein infusion. Previous studies have shown that 80% to 901 of hepatocytes are transduced with this dose of atLenovirus (Q. Li, M. A. Kay, M. Finegold, L. D. Stratford-Perricaudet, S. L. C. Woo (1993) *Human Gene Therapy* 4, 403).

Murine muCTLA4Ig or L6 (placebo) were diluted in pyrogen free physiologic saline and administered in 200 to 400 μl by IP injection. Blood samples were obtained by retroorbital technique. Animals were sacrificed by cervical dislocation.

The construction, production and purification of the recombinant E1 deficient Ad5 vector (Ad/RSVhAAT) was as described (Kay et al. Hepatology 21:815–819 (1995)). A single recombinant virus preparation was used for L6 controls and muCTLA4Ig experimental animals. All virus preparations were found to be negative for the presence of contaminating wildtype virus as described (D. Barr et al. (1995) Gene Therapy 2:151–155).

C3H/HeJ mice were infused with Ad/RSVhAAT an adenovirus that directs expression of human alpha 1-antitrypsin, in transduced hepatocytes, and treated with either muCTLA4Ig or L6 (a control monoclonal antibody).

Persistence of gene expression in individual animals was determined by periodic serum quantitation of human alpha 1-antitrypsin (hAAT).

In FIG. 1, sixteen female C3H/HeJ mice 6 to 8 weeks of age were infused with $5 \times 10^9$ pfu of Ad/RSVhAAT adenovirus by tail vein on day 0. In panels A and C, the animals received 200 μg of murine CTLA4Ig (IP) on day 2 (n=4, solid circles) or days 0, 2, 10 (n=4, open circles). Control animals received equivalent amounts of a control antibody (L6) on day 2 (n=4) (solid squares) or days 0, 2, 10 (open squares) (n=4).

FIG. 1 panels B and D were repeat experiments. Ten mice were infused with Ad/RSVhAAT adenovirus on day 0. Animals received either soluble CTLA4Ig (n=5, open circles) or L6 (n=5, open squares) on days 0, 2, 10. Periodic serum samples were analyzed for (A) hAAT, (B) hAAT (Kay et al. 1995, supra) or (C) CTLA4Ig, (D) CTLA4Ig by ELISA. Each line represents an individual animal. ELISA assays were performed in at least duplicate for each measurement.

Murine CTLA4Ig serum concentrations were performed by ELISA assay. Human B7-1-Ig (50 ng in 50 μl bicarbonate buffer pH 9.6) was coated onto 96-well Immulon-2 plates. The washed and blocked wells were plated with diluted serum samples or diluted standard muCTLA4Ig. After binding and washing, 50 μl (1/5000 dilution) of horseradish peroxidase labeled goat anti-mouse IgG2a Southern Biotechnology, Birmingham, Ala.) was incubated at room temperature for 1 hour. After washing, the horseradish peroxidase was detected using 3, 3', 5, 5' tetramethylbenzidine (Sigma). The reaction was stopped using 50 μl of 1N sulfuric acid. Absorbance at 450 nm (reference 630 nm) was performed using a microtiter plate reader (Biorad) and concentrations were determined using a linear regression of the standard curve. The sensitivity was 0.1 ng/ml.

FIG. 2 provides spleen proliferation assay results on days 4 (FIG. 2 panel A), 11 (FIG. 2 panel B) or 18 (FIG. 2 panel C) after the administration of Ad/RSVhAAT, splenocytes were isolated by hypotonic lysis and cultured as described in flat bottom 96 well plates (D. B. Lewis et al. (1991) *J. Exp. Med.* 173, 89).

Figure 2A:
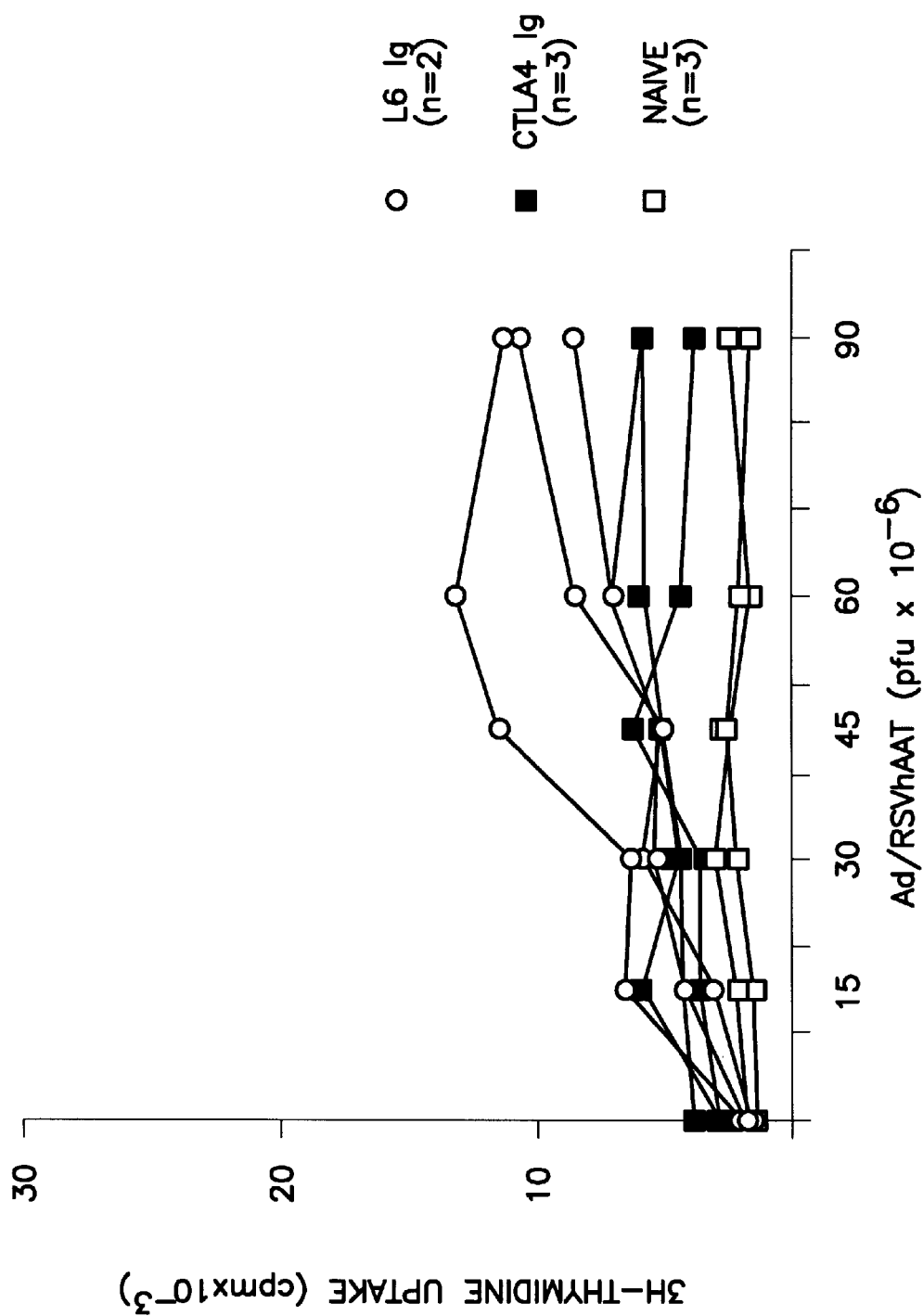
Figure 2B:
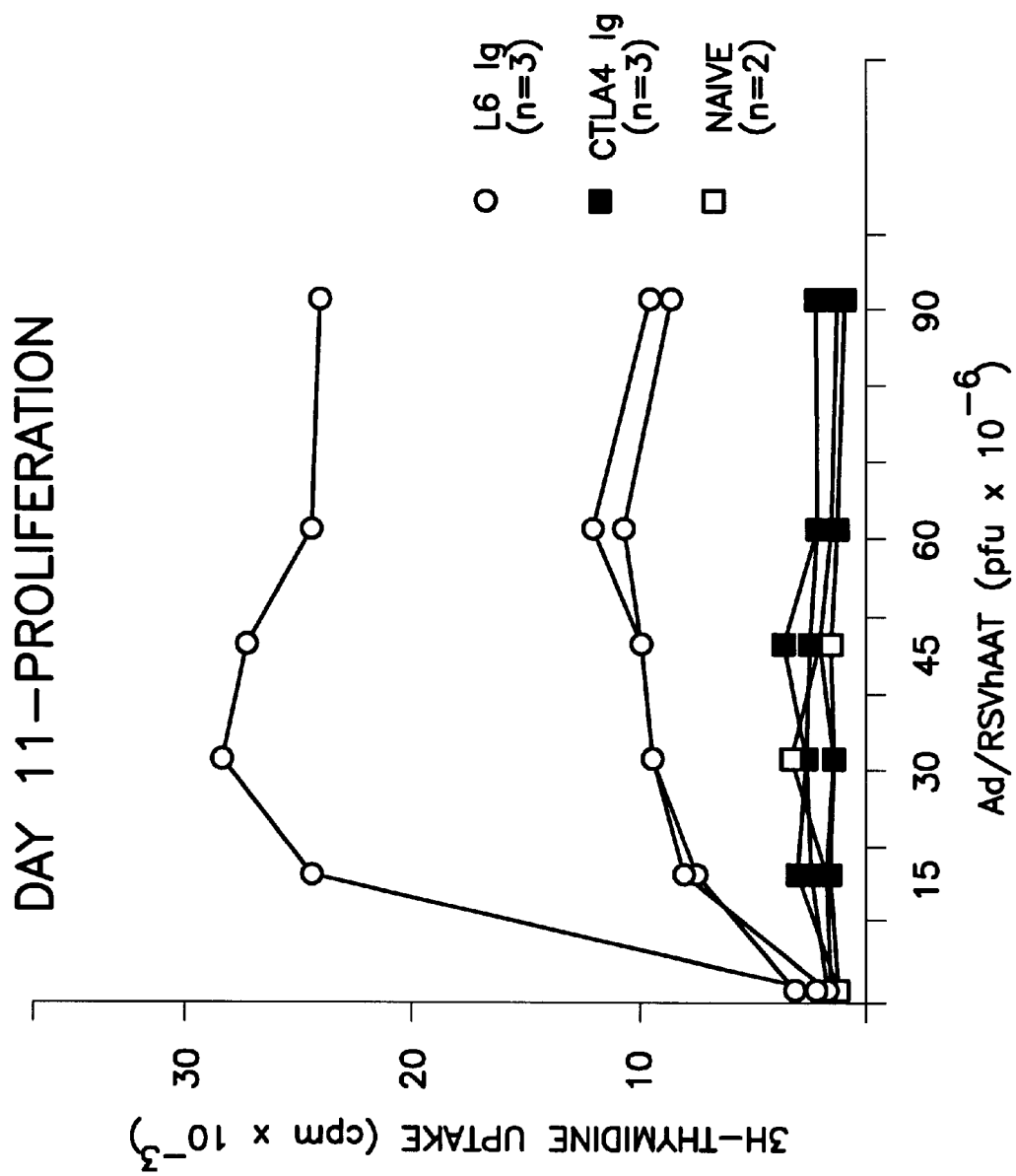
Figure 2C:
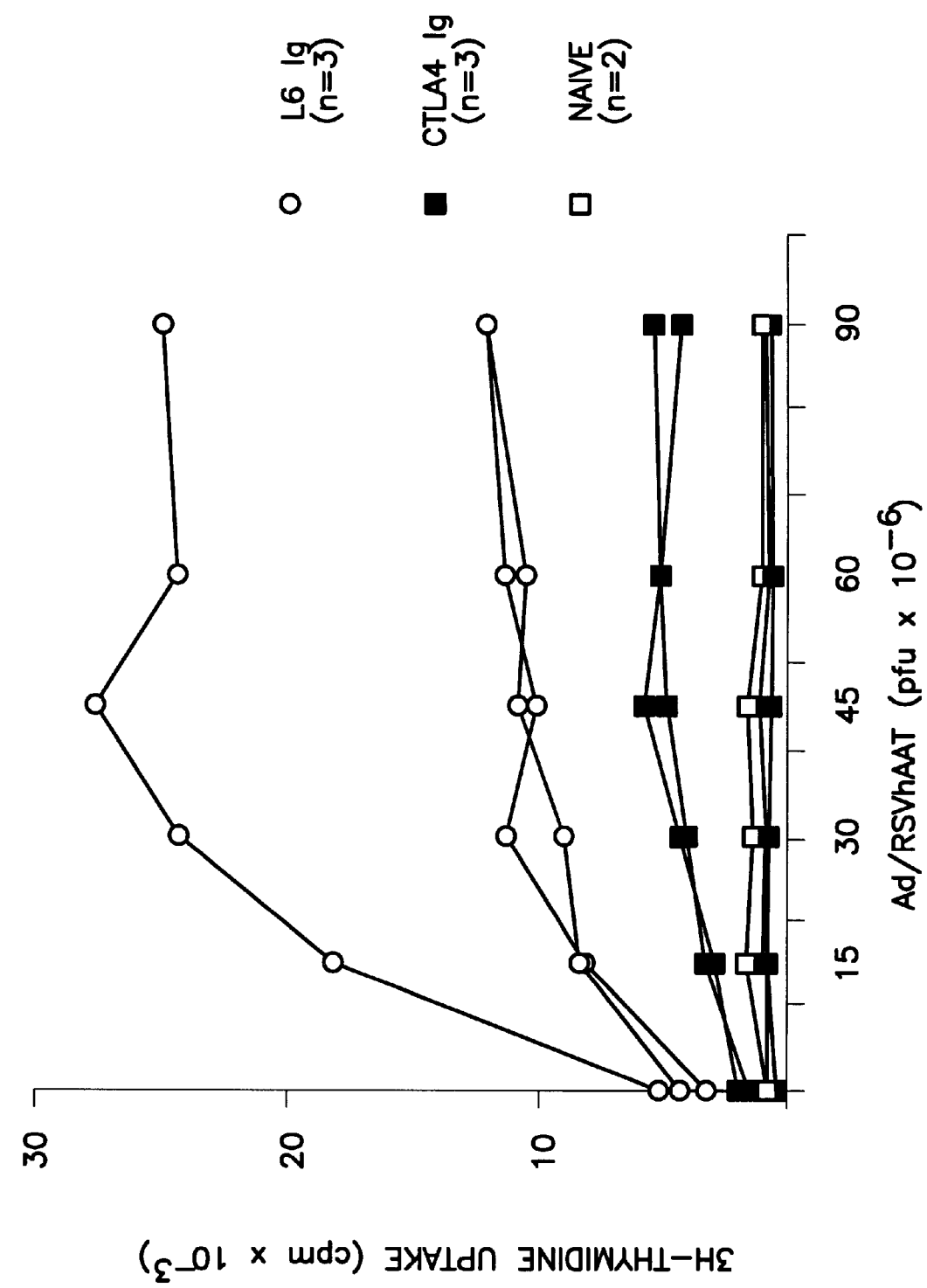
Figure 3A:
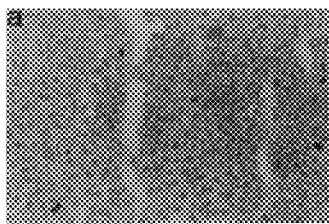
Figure 3B:
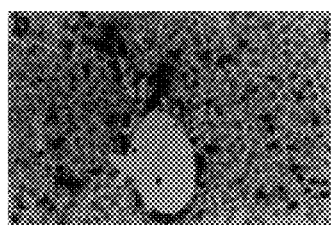
Figure 3C:
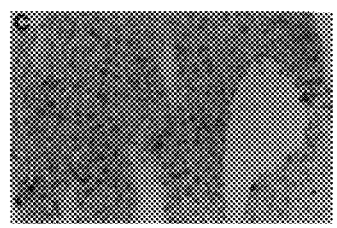
Figure 3D:
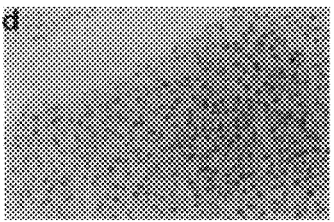
Figure 3E:
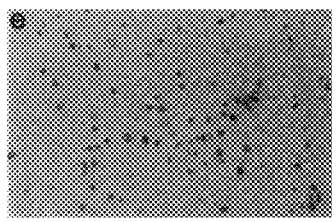
Figure 3F:

In FIGS. 2A–C, cells at a concentration of $3 \times 10^6$/ml were incubated with varying concentrations of UV inactivated Ad/RSVhAAT as indicated. Supernatants were harvested at 72 hours for lymphokine assays or cells were pulsed with $^3$H-thymidine and harvested 24 hours later for determination of proliferation.

Lymphokine assays involve determining murine interferon-γ by ELISA using the monoclonal antibodies R46A2 and XMG1.2 as capture and detection reagents respectively. Murine IL-4 was determined by ELISA using monoclonal antibody pairs from Pharmingen. Recombinant murine IFN-γ and IL-4 were used as standards in each assay.

In FIG. 3, animals were infused with $5 \times 10^9$ pfu of Ad/RSVhAAT on day 0. The animals were treated with either L6 (panels b and e) or muCTLA4Ig (panels c and f) on days 0, 2, 10. Liver from normal animals were processed in parallel (panels a and d). Frozen liver sections from the animals sacrificed on day 18 were incubated with anti-CD3 (panels a–c) or anti-CD8 (panels d–f) antibodies. Staining was with goat horseradish peroxidase conjugate anti-hamster (panels a–c) or anti-rat (panels d–f) antibody. Magnification is 50×.

Immunohistochemical staining was carried out on liver tissues that were frozen in OCT and sectioned. The following antibodies were used: CD3-biotin (1452C11, Pharmingen, San Diego, Calif.), CD 4 (GK1.5, American Type Culture Collection (ATCC)), CD8 (53–6.7 ATCC), NK (rabbit anti-asialoGM1. Dako), anti-class I-biotin (anti-H2K$^k$, 11–4.1 Pharmigen), anti-class II biotin (anti-I-E$^k$ 14.4–45, ATCC). Biotinylated antibodies were detected with streptavidin horseradish peroxidase conjugates as appropriate. Matched irrelevant rat or rabbit antibodies were used as controls for non-specific staining. The scoring system for portal inflammation was based on that described by R. G. Knodell et al., (1981) Hepatology 1,431.

Eight normal animals were used as controls and scored as 0. The experimental groups were scored based on relative staining using a 0 to 4 scale relative to the normal animals paralleling a scoring system used by others to grade portal inflammation (Yang et al. (1994) Immunity, supra). The average of the two scores for each liver section is listed.

Two mice, #14 and #23 had less than 50 ng/ml of serum HAAT probably due to an inadequate infusion of Ad/RSVhAAT virus. The numbers in parentheses represent the mean without animals 14 and 23 (NA=not available). The animals used are those shown in FIG. 2 and described herein.

Gene expression was greatly extended in animals that received CTLA4Ig compared to the controls (FIGS. 1A–D). All the L6 control animals (n=8) had a greater than 100-fold decline in serum HAAT concentration between 2 and 7 weeks (FIG. 1A) after adenovirus administration to values that were not above background; these data are similar to those seen in a previous study (D. Barr, supra). All the muCTLA4Ig treated animals maintained high levels of hAAT expression for at least 14 weeks (n=8), and 6 out of 8 mice expressed high levels of hAAT for >5 months, the length of the experiment (FIG. 1A). There was no difference in hAAT persistence in mice given 1 or 3 doses each of 200 μg of muCTLA4Ig.

Figure 1B:
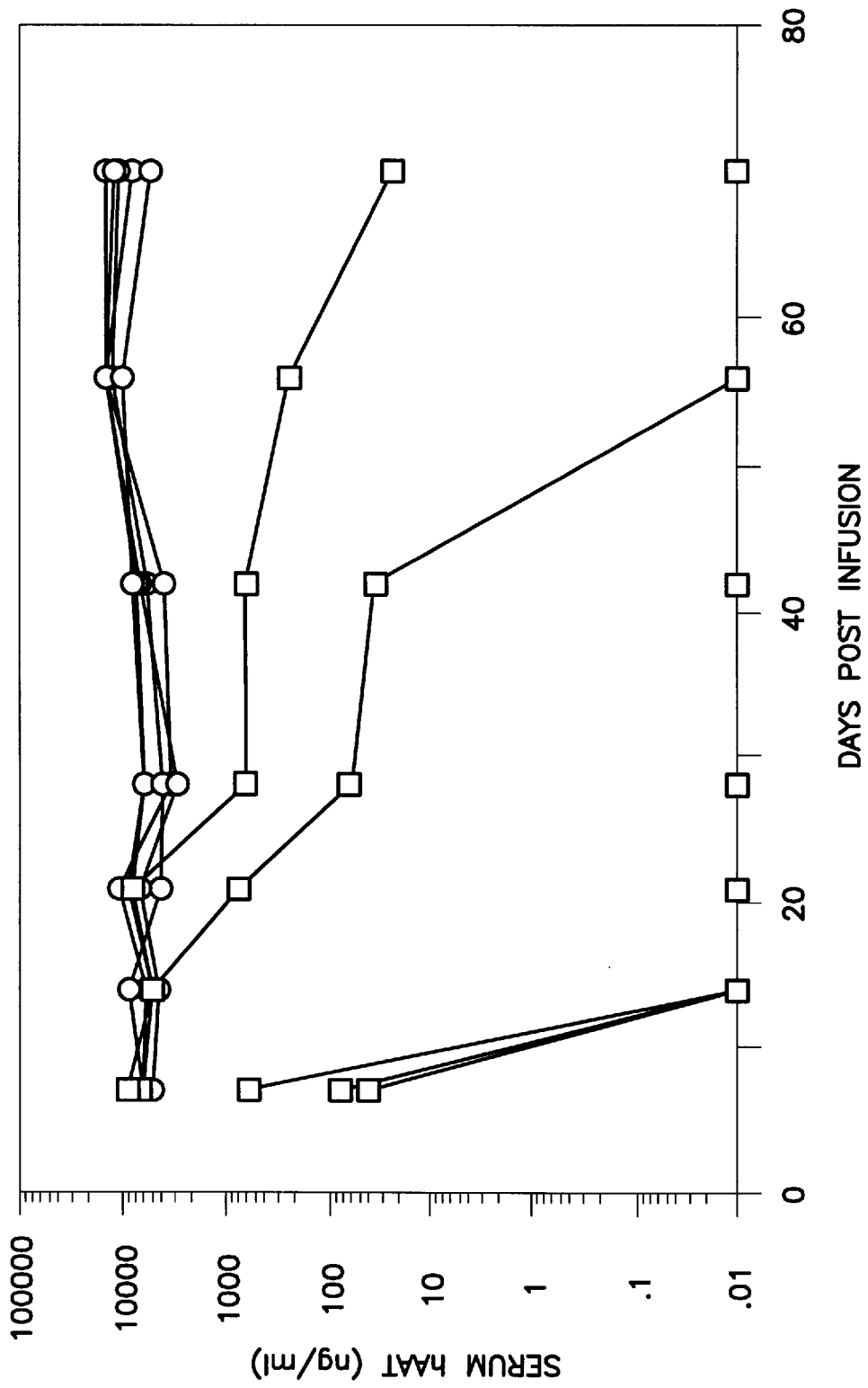

A second set of experiments presented in FIG. 1B gave similar results. Strikingly, the period of adenovirus-mediated gene expression was similar to that seen in previous studies in congenic C3H scid mice that lack antigen specific immunity (D. Barr, supra), and to the duration of adenovirus transduced beta-galactosidase expression observed in T-cell deficient nude mice (Y. Yang, H. C. J. Ertl, J. M. Wilson (1994) *Immunity* 1, 433; J. F. Englehardt, X. Ye, B. Doranz, J. M. Wilson (1994) *Proc. Natl. Acad. Sci. USA* 91, 6196).

Figure 1C:
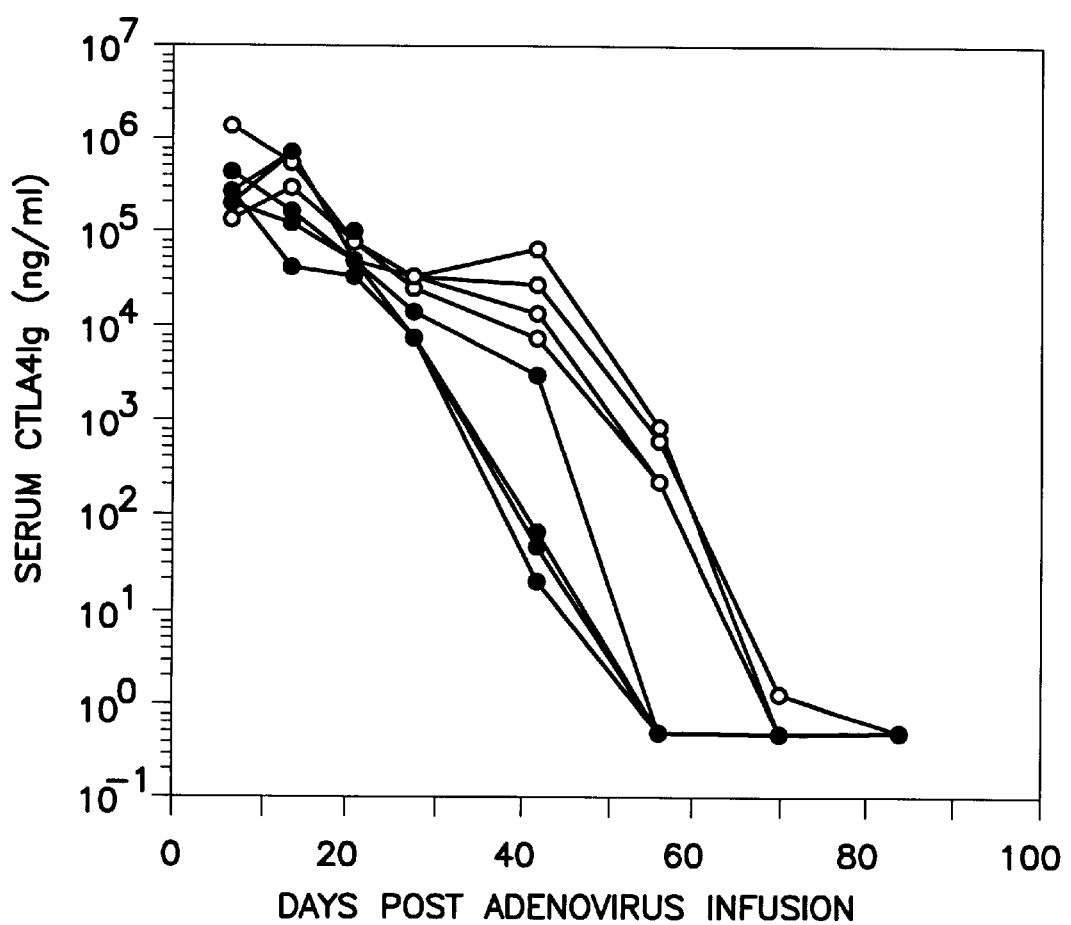
Figure 1D:
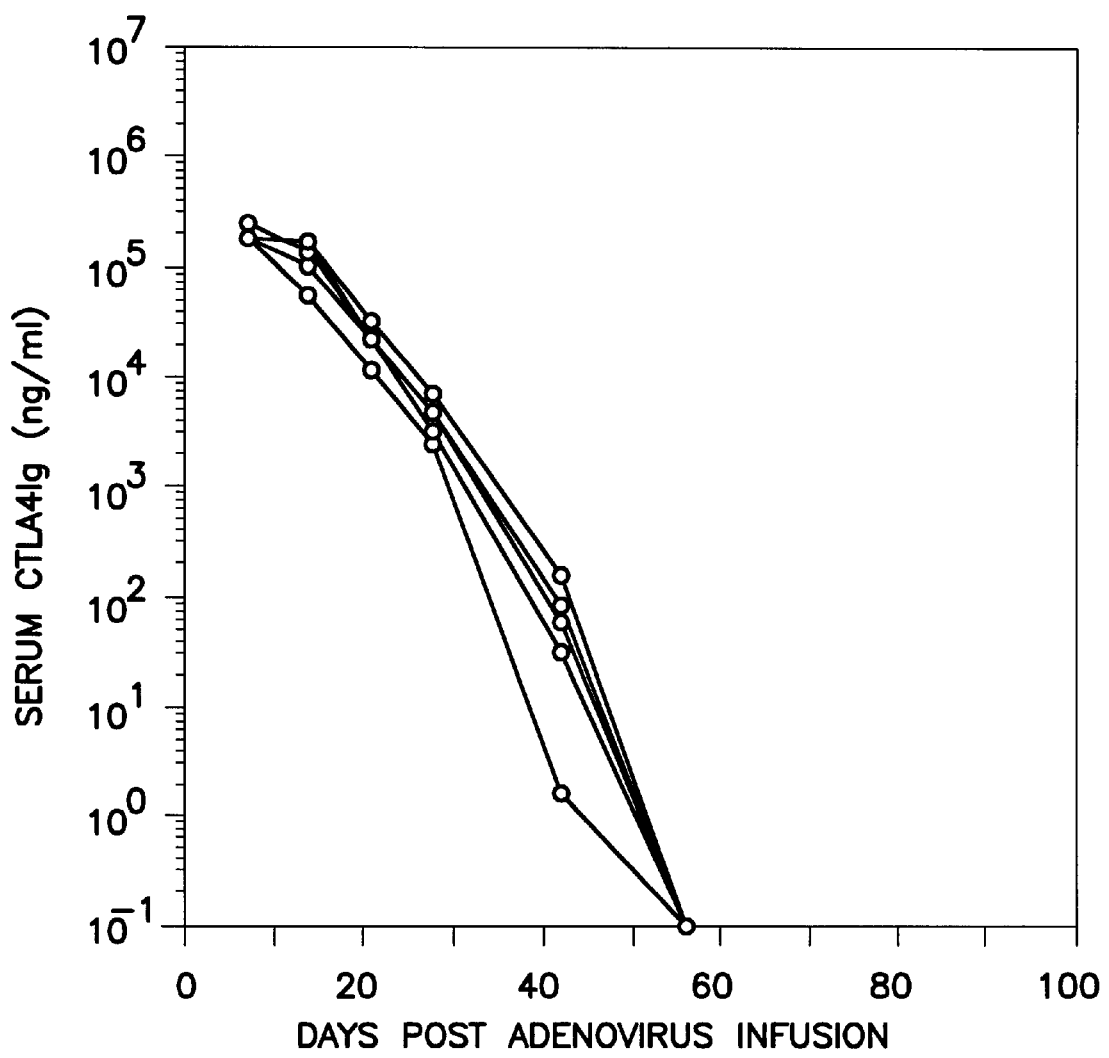

Long-term adenovirus mediated gene expression was not the result of persistent immunosuppression. Serum concentration of muCTLA4Ig fell dramatically from about 100 μg/ml to less than 10 ng/ml over a period of 40 to 70 days (FIGS. 1C and D). Successful immunosuppression by CTLA4Ig is associated with serum concentrations greater than 1 μg/ml.

The muCTLA4Ig treated animals were able to mount an immune response to a different antigen. To determine this, the muCTLA4Ig and L6 treated animals were challenged with a neo antigen, bacteriophage φX 174, 10 weeks after the initial adenovirus infusion (S. Nonoyama, F. O. Smith, I. D. Bernstein, H. D. Ochs (1993) *J. Immunol.* 150, 3817).

The bacteriophage φX174 was grown, harvested and purified as in Nonoyama et al. supra. $2.5 \times 10^8$ pfu in 200 μl was infused I.V. 10 and 14 weeks after adenovirus transduction. Phage neutralizing antibody titers were determined weekly for a total of 8 weeks post first phage infusion as described. The titers were expressed as Kv or rate of phage inactivation over time. In muCTLA4Ig and L6 treated mice, the mean Kv two weeks post primary was 2.2 (range 2.0 to 14) and 3.9 (range 1.5 to 33), respectively. Two weeks post secondary phage infusion the mean Kv for muCTLA4Ig treated animals was 49 (range 3.6 to 1043) and for L6 treated animals was 98 (range 15–1469). At this time point the percentage of IgG antibody varied between 70% and 100% in muCTLA4Ig treated mice and 50% to 100% in L6 treated animals.

T cell help is required for efficient antibody production including amplification and IgM to IgG isotype switch in response to bacteriophage φX174 (S. Nonoyama et al. (1993) *J. Exp. Med.* 178, 1097). Since T cell-dependent B cell responses are blocked by CTLA4Ig this provided a sensitive measure of residual muCTLA4Ig (B. K. Finck, P. S. Linsley, and D. Wofsy (1994) *Science* 265, 1225; P. S. Linsley and J. A. Ledbetter (1993) *Ann. Rev. Immunol.* 11, 191).

All muCTLA4Ig and L6 treated animals produced normal amounts of IgM and IgG neutralizing antibodies in response to primary and secondary bacteriophage φX174 immunization indicating the absence of biologically active muCTLA4Ig (S. Nonoyama, F. O. Smith, I. D. Bernstein, H. D. Ochs (1993) *J. Immunol.* 150, 3817).

The long-term persistence of hAAT gene expression from muCTLA4Ig treated animals suggested that inhibition of the costimulatory activation of T-cells was responsible for inhibiting cellular immunity directed against viral antigens. To determine whether T cell immunologic recognition of adenovirus antigens was inhibited with CTLA4Ig therapy, spleen cell proliferation assays were performed in animals transduced with Ad/RSVhAAT and treated with muCTLA4Ig or L6.

11 or 18 days after adenovirus infusion, mice were sacrificed and splenocytes isolated were stimulated with varying concentrations of Ad/RSVhAAT. Cell proliferation by adenovirus primed T-cells was assayed by 3H-thymidine uptake at 72 hours (FIG. 2) On day 4 there was minimal 3H-thymidine incorporation in either group.

On days 11 and 18 dose-dependent, antigen-induced splenocyte proliferation was detected in L6 treated controls, but was absent or markedly reduced in the CTLA4Ig treated animals (FIGS. 2B and C). The responses in the muCTLA4Ig treated mice were similar to those observed in naive animals that did not receive adenovirus.

The impairment of the response in the muCTLA4Ig treated mice was specific, since proliferation in response to anti-CD3 stimulation was similar in muCTLA4Ig treated, LE treated and naive control mice.

Yang et al. found that the immune response to adenoviral vector transduced hepatocytes had the characteristics of a type 1 or TH1 lymphokine response, in that interferon-$\gamma$ and IL-2 but not IL-4 were produced by antigen-stimulated splenocytes (Y. Yang, H. C. J. Ertl, J. M. Wilson (1994) *Immunity* 1, 433). The preliminary data are consistent with this in that interferon-$\gamma$ was induced (>20 ng/ml) in Ad/RSVhAAT stimulated cultures from 5 of the 9 L6 treated mice, whereas IL-4 was not detected (<50 pg/ml). Neither interferon-$\gamma$ nor IL-4 was induced in antigen-stimulated cultures from muCTLA4Ig treated mice or naive control mice.

Consistent with the results of the in vitro assays, the T cell response to adenovirus transduced hepatocytes was markedly attenuated in vivo. In assays performed in parallel with the lymphocyte proliferation studies, liver sections from normal control animals and from mice which received Ad/RSVhAAT 4, 11 and 18 days earlier were examined.

To determine the nature of the cellular infiltrate, sections were reacted with a monoclonal antibody to CD3, which detects all T cells, with monoclonal antibodies to the CD4 and CD8 T cell subsets, class I and class II MHC and with a polyclonal antiserum to NK cells.

Representative sections reacted with antibodies to CD3 and CD8 are shown in FIG. 3 and all results are summarized in Table 1. There was little or no cellular infiltrate in either group after 4 days. However, after 11 and 18 days there was a robust (primarily periportal) infiltrate of T cells in the L6 animals but little or no infiltrate in mice that received muCTLA4Ig.

The T cells were predominantly of the CD8 subset. Induction of class II MHC expression was also diminished in the muCTLA4Ig treated group relative to the L6 treated group, but the results were more variable than for the T cell markers. There was little NK cell infiltration in either group. The animals that were transduced with adenovirus had increased hepatocellular staining for class I MHC regardless of whether they received CTLA4Ig or L6.

While cellular immunity is believed to limit the duration of adenovirus transduced gene expression, antibody-mediated, humoral immunity is believed to limit secondary adenovirus transduction (Y. Yang et al. (1994) *Proc. Natl. Acad. Sci., USA* 91, 4407; Y. Yang, H. C. J. Ertl, J. M. Wilson (1994) *Immunity* 1, 433; T. G. Smith et al. (1993) *Nature Genetics* 5, 397; Barr et al. supra).

When antibody production was determined in the mice shown in FIG. 1A, muCTLA4Ig was found to impede markedly but not ablate production of antibodies to the adenovirls vector.

As shown in Table 2, all L6 treated animals developed neutralizing antibodies to adenovirus by 4 weeks after the infusion, whereas the response was delayed and attenuated in the muCTLA4Ig treated mice. Nonetheless, 2 of the CTLA4Ig treated mice developed neutralizing titers greater than or equal to 16 by 10 weeks after infusion and only two of the mice failed to develop any detectable neutralizing antibody.

Neutralizing and isotype specific antibodies directed against adenovirus were determined from mice studied in FIGS. 1A and C. The neutralizing antibody and IgG2a titers are listed s the median reciprocal (1/x) titer. The range for each group is given in parenthesis (nd=not determined).

Neutralizing antibody titer measurements were modified from (D. Barr, supra). Briefly, $5 \times 10^4$ 293 cells were plated in 96 well plates. Serum samples were heat inactivated at 55° C. for 40 minutes and 100 ul serum (four fold) dilutions (least dilution was $1/16$) in DMEM/1% fetal calf serum were mixed with 10 $\mu$l of Ad.RSV$\beta$gal ($3 \times 10^5$ pfu) for 1 hour at 37° C. The mixture was layered onto the 293 cells for 60 minutes before replacing the virus mixture with fresh media. The cells were stained with $\beta$-gal 16 to 24 hours later and the titer was defined as the dilution that inhibits 75% staining of 293 cells. By this criteria, all the L6 controls that received adenovirus had neutralizing titers greater than or equal to $1/32$, whereas only two of the muCTLA4Ig mice had neutralizing titers that were equal to or greater than $1/16$. The serum from two muCTLA4Ig treated animals had no inhibition of $\beta$gal staining at a $1/16$ dilution, whereas the serum from four of these animals had less than 75% inhibition of $\beta$gal staining at a $1/16$ serum dilution, indicating the presence of low titer adenovirus neutralizing antibody. IgM, IgG1 and IgG2a antibodies were determined by coating wells of microtiter plates (Dynatech Immunolon) with the optimal amount (50 ng/well) of UV-inactivated Ad/RSVhAAT in carbonate buffer (pH 9.6). After the plates were blocked they were incubated sequentially with serum samples (diluted from 1:100 to 1:6400 for IgG1 and IgG2a, diluted 1:100 to 1:800 for IgM), then detected with horseradish peroxidase-conjugated goat antibodies to mouse IgGl, IgG2a (Southern Biotechnology) or IgM (Tago). The lowest dilution yielding an optical density >0.100 (IgG1 and IgG2a) or >0.050 (IGM) above that obtained with serum from naive control was defined as the titer.

Virtually all of the virus-specific antibody detected by isotype-specific ELISA at 6 and 10 weeks was Of the IgG2a isotype. Each of 8 L6 treated mice developed high titers of IgG2a antibodies. The IgG2a response was markedly diminished in the muCTLA4Ig treated mice, although 6 of 8 ultimately developed detectable antibody titers of $\geq 100$. One L6 treated mouse had measurable antibody of the IgG1 isotype (1:400) and one muCTLA4Ig treated mouse had measurable IgM antibody (1:400) detected on the 6 and 10 week samples. The IgG2a isotype predominance is consistent with a type I or TH1 lymphokine response by T cells, since such T cells produce interferon-$\gamma$, which favors the production of this isotype while inhibiting IgG1 production, whereas IL-4 produced by type II or TH2 T cells has the opposite effect (W. A. Paul and W. E. Seder (1994) *Cell* 76, 241; L. Nguyen, D. M. Krnipe and R. W. Finberg (1994) *J. Immunol.* 152, 478); these results are consistent with the lymphokine results presented above.

The preponderance of IgG2a antibodies in both groups of mice, albeit in much reduced amounts in the muCTLA4Ig treated group, suggests that this agent markedly attenuated but did not alter the nature of the humoral immune response that developed.

To determine whether the low levels of antibodies in muCTLA4Ig treated mice were sufficient to impair gene expression with a secondary adenovirus vector, another experiment similar to those shown in FIG. 1 was carried out. Nine weeks after the first administration of Ad/RSVhAAT (when muCTLA4Ig was no longer detectable), the animals received an infusion of Ad.RSVcFIX that expresses canine factor IX (M. A. Kay, et al. (1994) Proc. *Natl. Acad. Sci., USA* 91, 2353), with or without a second treatment with muCTLA4Ig.

None of the mice expressed canine factor IX. This most likely reflects neutralization of the adenoviral vector by low levels of antibody present in the muCTLA4Ig treated mice, despite continued expression of the initial gene product: hAAT.

The results from this study indicate that administration of muCTLA4Ig for a brief period near the time of systemic vector administration led to persistent adenovirus mediated gene expression. The transient immunosuppression by muCTLA4Ig markedly attenuated T cell infiltration into the liver, the principal target organ, in vivo and antigen-induced T cell responses assayed in vitro. It is likely that these effects on T cell reactivity are causally related to the long term persistence of adenovirus transduced hepatocytes, in contrast to immune-mediated clearance observed in controls.

This is the first report of substantive, therapeutic enhancement of adenovirus mediated gene expression in vivo. These results contrast markedly with the minimal enhancement of adenovirus mediated gene expression from the liver achieved with continuous daily administration of cyclosporin A (J. F. Englehardt, X. Ye, B. Doranz, J. M. Wilson (1994) *Proc. Natl. Acad. Sci. USA* 91, 6196).

The results most closely parallel those achieved with a persistent genetic defect in T cell or T cell and B cell function due to the nude, scid or RAG2 mutations (Yang et al. (1994) PNAS; Yang et al. (1994) Immunity; Barr et al., supra), which like the muCTLA4Ig treated mice, continued to express the transduced gene for >5 to 6 months, the duration of the periods of observation. Strikingly, the transient nature of the muCTLA4Ig induced immunosuppression required to achieve long term adenovirus mediated gene expression contrasts with the continuous immunosuppression provided by these genetic defects and suggests persistent gene expression may be achieved without long term immunosuppression and its resultant adverse effects. Despite inhibition sufficient to lead to long term expression of the transduced gene, secondary gene transduction was not possible.

This likely reflects the efficient neutralization of the secondary vector by low levels of residual circulating neutralizing antibodies. Other immunologic based therapies, possibly in combination with less antigenic adenovirus vectors (Englehardt et al., supra) may be necessary for the development of true antigenic tolerance that will allow for repeat systemic adenovirus delivery.

The liver is a quiescent tissue under normal conditions and it is not possible to accurately predict how long the nonchromosomal, nonintegrated adenovirus genome will persist in hepatocytes or other tissues in the absence of immune destruction. Studies comparing the persistence of adenovirus mediated gene expression in immunodeficient animals with immunocompetent animals undergoing immunotherapies such as the one described here will be helpful in determining the limitations imposed by the immune system on the duration of gene expression as compared to non-immune mechanisms of genome turnover. The results of the study are a major advancement towards using adenovirus for long-term gene expression in vivo and will be useful for developing future clinical gene therapy trials.

TABLE 1

Liver Cell Infiltrate Identification

| | # | CD3 | CD4 | CD8 | I | II | NK |
|---|---|---|---|---|---|---|---|
| | DAY 4 | | | | | | |
| L6 | 1 | 0 | 0 | 3 | 0 | 0 | 0 |
| L6 | 2 | 0 | 0 | 0 | 3 | 0 | 0 |
| L6 | 3 | 0 | 0 | 0 | 1.5 | 0 | 0 |
| L6 | 4 | 1.5 | 0 | 0 | 3 | 0 | 0 |
| L6 | 5 | 0 | 0 | 2 | 1.5 | 0 | 0 |
| | mean | 0.3 | 0 | 0.4 | 2.4 | 0 | 0 |
| CTLA4 | 6 | 0 | 0 | 0 | 1 | 1 | 0 |
| CTLA4 | 7 | 2 | 0 | 0 | 2.5 | 0 | 1 |
| CTLA4 | 8 | 0 | 0 | 1 | 2.5 | 0 | 0 |
| CTLA4 | 9 | 0 | 0 | 0 | 2 | 0 | 0 |
| CTLA4 | 10 | 0 | 0 | 0 | 1.5 | 0 | 0 |
| | mean | 0.4 | 0 | 0.2 | 1.9 | 0 | 0.2 |
| | DAY 11 | | | | | | |
| | # | CD3 | CD4 | CD8 | I | II | NK |
| L6 | 11 | 2 | 2.5 | 3 | 3 | 3 | 1.5 |
| L6 | 12 | 4 | 1.5 | 4 | 2.5 | 3 | 2.5 |
| L6 | 13 | 3 | 0 | 2 | 2.5 | 2 | 2 |
| L6 | 14 | 0 | 0 | 0 | 1.5 | 1.5 | 0 |
| L6 | 15 | 2.5 | 1.5 | 0 | 2.5 | 1.5 | 0 |
| | mean | 2.3 | 1.1 | 1.8 | 2.4 | 2.2 | 1.2 |
| | | (2.9) | (1.4) | (2.3) | (2.6) | (2.4) | (1.5) |
| CTLA4 | 16 | 0 | 0 | 0 | 1 | 1 | 0 |
| CTLA4 | 17 | 0 | 0 | 0 | 2 | 0 | 1 |
| CTLA4 | 18 | 1 | 0 | 0 | 2.5 | 2 | 1 |
| CTLA4 | 19 | 0 | 0 | 0 | 2 | 2 | 0 |
| CTLA4 | 20 | 0 | 0 | 0 | 2 | 1 | 1 |
| | | 0.2 | 0 | 0 | 1.9 | 1.2 | 0.6 |
| | DAY 18 | | | | | | |
| | # | CD3 | CD4 | CD8 | I | II | NK |
| L6 | 21 | 4 | 2.5 | 3 | 3 | 2 | 1 |
| L6 | 22 | 4 | 1 | 3 | 2.5 | 2.5 | 0 |
| L6 | 23 | 0 | 0 | 0 | 0 | 0 | 0 |
| L6 | 24 | 2 | 1.5 | 2 | 1.5 | 2 | 0 |
| L6 | 25 | 3 | 2 | 2.5 | 3 | 2 | 0 |
| | mean | 2.6 | 1.4 | 2.1 | 2.0 | 1.7 | 0.2 |
| | | (3.3) | (1.8) | (2.6) | (2.5) | (2.1) | (0.3) |
| CTLA4 | 26 | 0 | 0 | 0 | 2.5 | 0 | 1 |
| CTLA4 | 27 | 0 | 0 | 0 | 2.5 | 0 | 1 |
| CTLA4 | 28 | 0 | 0 | 0 | 1.5 | 2 | 0 |
| CTLA4 | 29 | 0 | 0 | 0 | 1.0 | 2.5 | 0 |
| CTLA4 | NA | | | | | | |
| | mean | 0 | 0 | 0 | 1.9 | 1.1 | 0.5 |

TABLE 2

| TYPE OF ANTIBODY | WEEK 4 | | WEEK 6 | | WEEK 10 | |
|---|---|---|---|---|---|---|
| | CTLA4Ig | L6 | CTLA4Ig | L6 | CTLA4Ig | L6 |
| Neutralizing | <16 (<16) | 32 (16–128) | <16 (<16–64) | 64 (16–128) | <16 (<16–64) | 32 (<16–64) |
| IgG2a ELISA | nd | nd | <100 (<100–400) | 6400 (1600 > 6400) | 100 (<100–6400) | 6400 (1600 > 6400) |

EXAMPLE 2
Preparation of CTLA4Ig Adenoviruses:

The constructs Ad/RSV-CTLA4Ig(mu) -BPA and Ad/RSV-CTLA4Ig(hu)-BPA were prepared by directional cloning of gene clean purified Hindlll/Xbal human and murine CTLA4Ig fragments into the Hindlll/Xbal sites between the RSV (Rous sarcoma virus LTR) promoter and BPA (Bovine polyadenylation signal) of the left-end adenovirus plasmid Ad/RSV-BPA (derived from PXCJL.1). Each of these two left-end adenovirus plasmids were then co-transfected with the right-end adenovirus plasmid pBHG10 using a standard Calcium Phosphate transfection protocol, and the recombinant adenovirus was rescued after 14–18 days. The adenovirus was then plaque purified, and clones for each found to express the human and murine CTLA4Ig protein by ELISA assay, were expanded and purified over two Cesium Chloride gradients.

The Bicistronic HAAT (Human alpha-1-antitrypsin protein)/human and murine CTLA4Ig left end vectors were prepared by cloning the purified, T4 DNA polymerase polished, Hindlll/Xbal Human and Murine CTLA4Ig fragments into the unique Small site between the Poliovirus internal ribosome binding sequence (POLIO) and BPA in the pKS plasmid containing RSV-HAAT-POLIC) (SMAI)-BPA. Recombinants found to contain the CTLA4 fragments in the appropriate orientation were digested with Xhol and the RSV-HAAT-BPA-CTLA4Ig-BPA purified fragment cloned into the unique Xhol site in the pXCJL.1 left-end adenovirus plasmid (same back-bone as the Ad/RSV left end plasmid). Recombinant viruses are currently being rescued as described above.

$4 \times 10^9$ PFU of the Ad/RSV-CTLA4Ig(mu)-BPA recombinant adenovirus has been injected into the tail veins of three C3H mice and produced maximum serum levels of 2369, 2:L68, and 1762 ng/ml of plasma 3 weeks after injection. The Ad/RSV-CTLA4Ig(hu)-BPA adenovirus has been injected into several C3H mice and plasma levels of CTLA4Ig(hu) evaluated.

EXAMPLE 3

The humoral immunity directed against the adenovirus vector is blunted but not eliminated with CTLA4Ig administration. Thus, we used CTLA4Ig with antiCD40 ligand (MR1) to prolong gene expression and allow for secondary gene transfer.

The animals received adenovirus (Ad/RSV-hAAT, $5 \times 10^9$ pfu) on day 0, CTLA4Ig (200 μg) on days 0, 2, 10 and MR1 (250 μg) on days 0, 2, 4, and 6. L6 (placebo) was diluted in pyrogen free physiologic saline and administered in 200–400 μl by IP.

All of the animals have persistent gene expression. All of the L6 controls went to 0 gene expression by 2–6 weeks. Half of the animals have no detectable neutralizing antibodies. Similarly, half the animals could be transduced a second time with a recombinant adenovirus vector (Ad.RSV-cFIX). Thus, combined MR1/CTLA4Ig therapy has potential to prolong gene expression and allow for secondary gene transfer. The latter is probably the result of blocking humoral immunity.

Table 3 provides data showing that at least with half the animals one is able to give a second dose of virus and have successful adenoviral gene transfer.

TABLE 3

| A Mouse Number | B Gene expression from first Ad.RSVhAAT infusion (0 → wk 10) Serum HAAT level | C Gene expression from second Ad.RSVcFIX on week 14 (6 days after infusion) Serum CFIX level | D Neutralizing AdV antibody titers Ab Titer | E Ab Titer |
|---|---|---|---|---|
| 2 2152-combined | 1535 | 217 | <1:16 | 1:16 |
| 3 2153-combined | 1269 | <200 | <1:16 | 1:16 |
| 4 2154-combined | 1402 | 432 | <1:16 | <1:16 |
| 5 2156-combined | 435 | <200 | <1:16 | 1:16 |
| 6 2157-combined | 150 | 210 | <1:16 | 1:64 |
| 7 2158-combined | 1671 | 914 | <1:16 | <1:16 |
| 8 2166-CTLA4Ig | 129 | <200 | <1:16 | 1:64 |
| 9 2173-MR1Ig | 1326 | <200 | 1:16 | 1:256 |
| 10 2175-MR1Ig | 1510 | <200 | <1:16 | <1:16 |
| 12 2184-L6 | 0.5 | 0 | 1:256 | >1:1024 |

What is claimed is:

1. A method for inhibiting an immune response directed against an adenoviral vector in a subject, the method comprising introducing an adenoviral vector encoding a gene of interest into the subject and administering a sufficient amount of a soluble CTLA4 molecule and an antiCD40 ligand to the subject effective to inhibit the immune response directed against the adenoviral vector thereby increasing gene expression of the gene of interest in the subject.

2. The method of claim 1, wherein the subject is an animal.

3. The method of claim 2, wherein the animal is a human.

4. The method of claim 1, wherein the gene of interest encodes a protein.

5. The method of claim 4, wherein the protein is a cytokine and is selected from the group consisting of PDGF, EGF, FGF, IGF TGF, IL, INF and TNF.

6. The method of claim 1, wherein the soluble CTLA4 molecule is a functional CTLA4 molecule which binds a B7 antigen expressed on activated B cells.

7. The method of claim 1, wherein the soluble CTLA4 molecule is CTLA4Ig.

8. The method of claim 1, wherein the soluble CTLA4 molecule is joined to a non-CTLA4 protein sequence.

9. The method of claim 8, wherein the non-CTLA4 protein sequence is an Fc portion of an immunoglobulin molecule.

10. A method of claim 1, wherein the antiCD40 ligand is MR12.

* * * * *